US008007849B2

(12) United States Patent
Pei et al.

(10) Patent No.: US 8,007,849 B2
(45) Date of Patent: Aug. 30, 2011

(54) UNSATURATED CYCLIC AND ACYCLIC CARBAMATES EXHIBITING TASTE AND FLAVOR ENHANCEMENT EFFECT IN FLAVOR COMPOSITIONS

(75) Inventors: Tao Pei, Morganville, NJ (US); Mark L. Dewis, Matawan, NJ (US); Adam Jan Janczuk, Parlin, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 1566 days.

(21) Appl. No.: 11/304,151

(22) Filed: Dec. 14, 2005

(65) Prior Publication Data

US 2007/0134389 A1 Jun. 14, 2007

(51) Int. Cl.
*A23L 1/22* (2006.01)

(52) U.S. Cl. ............ 426/534; 426/3; 426/590; 426/648; 426/649; 426/650

(58) Field of Classification Search .............. 426/3, 534, 426/536, 537, 538, 590, 648, 649, 650
See application file for complete search history.

(56) References Cited

U.S. PATENT DOCUMENTS 2,598,664 A 6/1952 Kropa
(Continued)

FOREIGN PATENT DOCUMENTS

| | | |
|---|---|---|
| BE | 626980 | 7/1963 |
| DE | 2061051 | 12/1971 |
| EP | 1 291 342 A1 | 3/2003 |
| GB | 1016826 | 1/1966 |
| GB | 1537991 | 1/1979 |
| WO | WO2004106305 | 12/2004 |

OTHER PUBLICATIONS

Harry Tilles: "Thiolcarbamates. Preparation and Molar Refractions" J. Am. Chem. Soc., 1959, vol. 81, pp. 714-727.

(Continued)

*Primary Examiner* — Leslie Wong
(74) *Attorney, Agent, or Firm* — Elizabeth M. Quirk; XuFan Tseng; Joseph F. Leightner

(57) ABSTRACT

The present invention relates to novel compounds having sweet, salt or umami taste enhancement qualities. These compounds have the structure:

Structure I

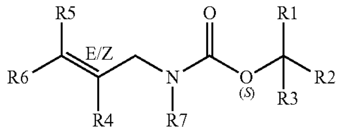

Structure II

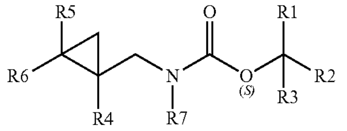

where $R^1$ is H or methyl;

$R^2$ is selected from the group consisting of H, C1-C4 alkyl, alkenyl;

$R^3$ is selected from the group consisting of H, phenyl, C1-C10 straight or branched chain alkyl, alkenyl, alkynyl, alkyldienyl, acyclic or containing no more than one ring, which contains no more than a total of five heteroatoms selected from F, O, S, N, and P; and if $R^1$=H, $R^2$ and $R^3$ taken together can represent

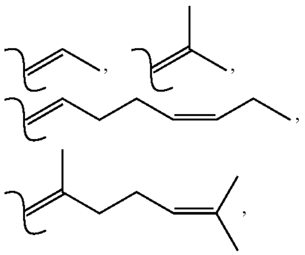

cyclopropyl, cyclobutyl, cyclopentyl, cyclopentenyl, cyclohexyl, or cyclohexenyl, which contains no more than two of each heteroatom selected from N, O, and S;

or if $R^1$, $R^2$ and $R^3$ taken together can represent one, or two aromatic rings, which contain no more than three of each heteroatom selected from F, N, S, and O.

$R^4$ is selected from the group consisting of H, methyl or ethyl;

$R^5$ is selected from the group consisting of H, methyl and ethyl;

$R^6$ is selected from the group consisting of H, C1-C9 straight or branched chain alkyl, alkenyl, alkyldienyl, acyclic or containing no more than one ring;

except for in the case of structure 1 when if $R^4$=H or methyl and $R^5$=H or methyl, $R^6$ as described above and phenyl;

or when $R^4$, $R^5$, and $R^6$ taken together can be equal to

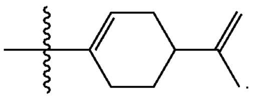

$R^7$ is selected from the group consisting C1-C4 alkyl, or alkenyl.

16 Claims, No Drawings

U.S. PATENT DOCUMENTS

| | | | | |
|---|---|---|---|---|
| 2,798,885 | A | 7/1957 | Ensslin et al. | |
| 3,284,461 | A | 11/1966 | Wilbert et al. | |
| 3,480,663 | A | 11/1969 | Thiele et al. | |
| 3,704,236 | A | 11/1972 | Tilles et al. | |
| 3,776,936 | A | 12/1973 | Singhal et al. | |
| 3,888,888 | A | 6/1975 | Pallos et al. | |
| 3,898,250 | A | 8/1975 | Schwartz et al. | |
| 4,997,672 | A | 3/1991 | DeSimone et al. | |
| 5,288,510 | A | 2/1994 | Gregory et al. | |
| 6,541,050 | B1 | 4/2003 | Bonorden et al. | |
| 2003/0091721 | A1 | 5/2003 | Ohta et al. | |
| 2003/0229102 | A1 | 12/2003 | Knobelsdorf et al. | |
| 2004/0142090 | A1 | 7/2004 | Goral | |
| 2005/0084506 | A1 * | 4/2005 | Tachdjian et al. | 424/400 |

OTHER PUBLICATIONS

M. Muhlstadt et al.: "Regiochemie der elektrophilen Cyclofunktionalisierung beta, gamma-ungesattigter Carbamidsaureester mit Brom—Synthese von Oxazolidin-2-onen und Tetrahydro-2H-1,3-oxazin-2-onen" J. Prakt. Chem., 1986, vol. 328, No. 2, 1986, pp. 163-172.

Database Beilstein Database accession No. 5500402, 5496510, 2078218, 2080321, 2086329.

Database Beilstein Database accession No. 9697432, 9697525 Dubowchik, G.M. et al.: Bioorg. Med. Chem. Lett. 14(12), 2004, pp. 3147-3150.

Database Beilstein Database accession No. 5849809, 5849468, 5849469, 4382051.

Database Beilstein Database accession No. 1766413 Olah et al.: J. Org. Chem. 22, 1957, p. 979.

Database Beilstein Database accession No. 3049706, 3049116 Ludwig, B.J. et al.: J. Med. Chem. 12(3), 1969, p. 462-472.

Database Beilstein Database accession No. 4426132, 4443659, 4672226, 4672227.

Baizhan Liu: "Analysis of volatile constituents of mustard paste by gas chromatography/mass spectrometry with solid-phase microextraction and simultaneous distillation and extraction" FENXI HUAXUE, 2000, vol. 28, No. 12, pp. 1489-1492.

EPO Search Report.

* cited by examiner

UNSATURATED CYCLIC AND ACYCLIC CARBAMATES EXHIBITING TASTE AND FLAVOR ENHANCEMENT EFFECT IN FLAVOR COMPOSITIONS

FIELD OF THE INVENTION

Unsaturated cyclic and acyclic carbamate compounds having sweet, salt or umami taste and flavor enhancement quality.

BACKGROUND OF THE INVENTION

The term Umami, from the Japanese word to describe savory or meaty, is the term used to describe the unique overall fullness, savory or salivatory taste of food. Materials that exhibit this taste quality generally potentiate the intensity of glutamate solutions and this is one important characteristic of umami taste. It is increasingly becoming recognized as the fifth sense of taste, the others being sour, sweet, salt and bitter. Compounds traditionally described as possessing this character are monosodium glutamate (MSG), protein hydrolysates, some amino acids and certain nucleotides and phosphates.

MSG is the most widely used material as a 'taste enhancer' where it synergizes the perception of 'savory' ingredients, but has also been alleged to cause allergic reaction to a proportion of the population.

Among other chemical compounds, several nucleotides have also been described to exhibit the umami effect including Adenosine 5'-(trihydrogen diphosphate), 5'-Cytidylic acid (5'-CMP), 5'-Uridylic acid (5'-UMP), 5'-Adenylic acid (5'-AMP), 5'-Guanylic acid (5'-GMP), 5'-Inosinic acid (5'-IMP) and the di-sodium salts of 5'-Guanylic acid and 5'-Inosinic acid.

Recent literature cites an extensive range of other organic compounds as taste active components of mixtures shown to give the umami taste effect. These include but are not necessarily limited to: organic acids such as succinic acid, lactic acid, saturated straight chain aliphatic acids of six, eight, fourteen, fifteen, sixteen, and seventeen carbon chain lengths, Z4,Z7, Z10,Z13,Z16,Z19-docosahexaenoic acid, Z5,Z8, Z11,Z14,Z17-eicosapentaenoic acid, Z9,Z12, Z16, Z19-octadecadienoic acid, Z9-octadecenoic acid, glutaric acid, adipic acid, suberic acid, and malonic acid. Amino acids having umami effects reported in the literature include glutamic acid, aspartic acid, threonine, alanine, valine, histidine, praline, tyrosine, cystine, methionine, pyroglutamic acid, leucine, lycine, and glycine. Dipeptides possessing umami properties include Val-Glu and Glu-Asp.

Other miscellaneous compounds having umami properties include alpha-amino adipic acid, malic acid, alpha-aminobutyric acid, alpha-aminoisobutyric acid, E2,E4-hexadienal, E2,E4-heptadienal, E2,E4-octadienal, E2,E4-decadienal, Z4-heptenal, E2,Z6-nonadienal, methional, E3,E5-octadien-2-one, 1,6-hexanediamine, tetramethylpyrazine, trimethylpyrazine, cis-6-dodecen-4-olide, glutamate glycoconjugates, fish sauce blended with anchovy paste (U.S. Patent Application 2003/0142090) and a number of naturally occurring amino-acids.

Additionally, a variety of molecules are known by those skilled in the art to provide salt enhancement, these include but are not limited to Adenosine 5'-(trihydrogen diphosphate), 5'-Cytidylic acid (5'-CMP), 5'-Uridylic acid (5'-UMP), 5'-Adenylic acid (5'-AMP), 5'-Guanylic acid (5'-GMP), 5'-Inosinic acid (5'-IMP) and the di-sodium salts of 5'-Guanylic acid and 5'-Inosinic acid, (+)-(S)-Alapyridaine (chemical name N-(1-Carboxyethyl)-6-hydroxymethylpyridinium-3-ol), succinic acid, cetylpyridium chloride, bretylium tosylate, various polypeptides, mixtures of calcium salts of ascorbic acid, potassium chloride, calcium chloride, magnesium chloride, arginine ammonium chloride, alpha-amino acids and their corresponding hydrogen chloride, ammonium and sodium salts and a number of natural plant extracts. Uses of these materials are described in various U.S. Pat. Nos. 4,997,672; 5,288,510; 6,541,050, U.S. Patent Application 2003/0091721 and Eur. Pat. Appl. 2003/1291342.

Additionally, choline chloride has been shown to enhance salt and increase palatability of sodium chloride reduced systems, Physiol Behay. 1994, 55(6), 1039-46.

In addition to this work, our work has included the identification of new flavor materials described in U.S. Ser. No. 10/919,631 filed on Aug. 17, 2004, now U.S. Pat. No. 7,329, 767; U.S. Ser. No. 10/861,751 filed on Jun. 4, 2004, now U.S. Pat. No. 7,098,350; and U.S. Ser. No. 10/783,652 filed Feb. 20, 2004, now U.S. Pat. No. 7,632,531.

Despite these disclosures there is an ongoing need for new flavor ingredients particularly those that exhibit advantageous properties for flavor enhancement or modulation, or more preferably the lowering of MSG and/or salt levels in foodstuffs.

SUMMARY OF THE INVENTION

The present invention relates to novel compounds and a process for augmenting or imparting a flavor enhancement effect or modifying the perception of one or more of the five basic taste qualities sweet, sour, salt, bitter and umami, to a foodstuff, chewing gum, medicinal product, toothpaste, alcoholic beverage, aqueous beverage, snack, sauce or soup comprising the step of adding to a foodstuff, chewing gum, medicinal product, toothpaste, alcoholic beverage, aqueous beverage, snack, sauce or soup a flavor enhancement or modification of basic taste quality augmenting, enhancing or imparting quantity and concentration of at least one unsaturated acyclic or cyclic carbamate defined according to the structures:

Structure I

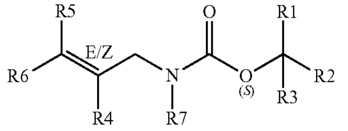

Structure II

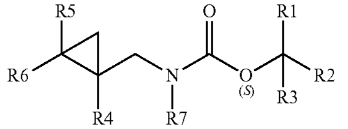

where $R^1$=H or methyl;

$R^2$ is selected from the group consisting of H, C1-C4 alkyl, alkenyl;

$R^3$ is selected from the group consisting of H, phenyl, C1-C10 straight or branched chain alkyl, alkenyl, alkynyl, alkyldienyl, acyclic or containing no more than one ring, which contains no more than a total of five heteroatoms selected from F, O, S, N, and P;

and if $R^1$=H, $R^2$ and $R^3$ taken together can represent

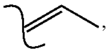,

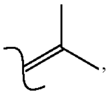,

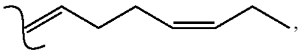,

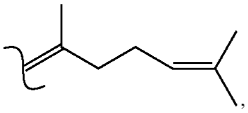, cyclopropyl, cyclobutyl, cyclopentyl, cyclopentenyl, cyclohexyl, or cyclohexenyl, which contains no more than two of each heteroatom selected from N, O, and S;

or if $R^1$, $R^2$ and $R^3$ taken together can represent one, or two aromatic rings, which contain no more than three of each heteroatom selected from F, N, S, and O.

$R^4$ is selected from the group consisting of H, methyl or ethyl;

$R^5$ is selected from the group consisting of H, methyl and ethyl;

$R^6$ is selected from the group consisting of H, C1-C9 straight or branched chain alkyl, alkenyl, alkyldienyl, acyclic or containing no more than one ring;

except for in the case of structure 1 when if $R^4$=H or methyl and $R^5$=H or methyl, $R^6$ as described above and phenyl;

or when $R^4$, $R^5$, and $R^6$ taken together can be equal to

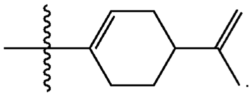.

$R^7$ is selected from the group consisting C1-C4 alkyl, or alkenyl.

As used herein compounds described in Structures I and II will be referred to as "cyclopropylic carbamates".

In addition to the novel compounds and the use of the compounds to enhance the taste of foodstuffs by the incorporation of the above ingredients and others set forth in this specification in foodstuff and other materials.

DETAILED DESCRIPTION OF THE INVENTION

The formula set forth above describes a general class of novel materials that we have found to enhance the flavor characteristics of food.

In a preferred embodiment of the invention the carbamates have the structure set forth below:

Structure III

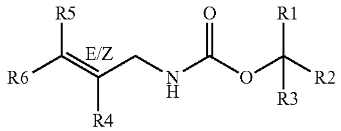

where $R^1$=H or methyl;

$R^2$ is selected from the group consisting of H, C1-C4 alkyl, and alkenyl;

$R^3$ is selected from the group consisting of H, phenyl, C1-C10 straight or branched chain alkyl, alkenyl, alkynyl, alkyldienyl, acyclic or containing no more than one ring, which contains no more than a total of five heteroatoms selected from F, O, S, N, and P;

or if $R^1$=H, $R^2$ and $R^3$ taken together can represent

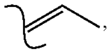,

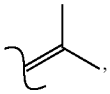,

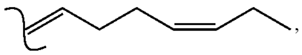,

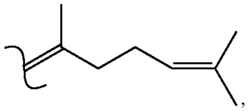, cyclopropyl, cyclobutyl, cyclopentyl, cyclopentenyl, cyclohexyl, or cyclohexenyl, and contain no more than two of each heteroatom selected from the group N, O, and S;

or if $R^1$, $R^2$ and $R^3$ taken together can represent one, or two aromatic rings, and contain no more than three of each heteroatom selected from the group F, N, S, and O.

$R^4$ is selected from the group consisting of H, methyl or ethyl;

$R^5$ is selected from the group consisting of H, methyl and ethyl;

$R^6$ is selected from the group consisting of H, C1-C9 straight or branched chain alkyl, alkenyl, alkyldienyl, acyclic or containing no more than one ring;

except for in the case of structure 1 when if $R^4$=H or methyl and $R^5$=H or methyl, $R^6$ as described above and phenyl;

or when $R^4$, $R^5$, and $R^6$ taken together can be equal to

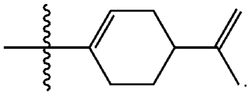.

In a highly preferred embodiment the carbamates have the structure set forth below:

Structure IV

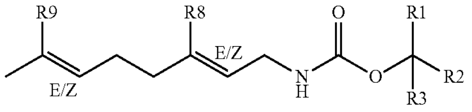

where $R^1$=H or methyl;

$R^2$ is selected from the group consisting of H, C1-C4 alkyl, alkenyl;

$R^3$ is selected from the group consisting of H, phenyl, C1-C9 straight or branched chain alkyl, alkenyl, alkyldienyl, and contains no more than two of each heteroatom selected from the group F, O, and N; or if $R^1$=H, $R^2$ and $R^2$ taken together can represent

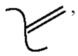,

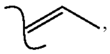,

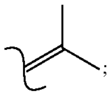;

$R^8$ is selected from the group consisting of H or methyl; and $R^9$ is selected from the group consisting of H or methyl.

These compounds and uses thereof have been found beneficial in augmenting or imparting an olfactory effect taste enhancement or somatosensory effect to a foodstuff, chewing gum, medicinal product, toothpaste, alcoholic beverage, aqueous beverage, snack, sauce or soup particularly providing a (a) umami taste, (b) salt effects, (c) flavor enhancement, and (d) preferred overall flavor profile.

As used herein the most preferred compounds will be referred to hereinafter as carbamates.

In the following tables and as used in the specification, Me is understood to be a methyl group and Et is understood to be an ethyl group.

Our invention specifically relates to the novel compositions according to the Structure 3 above:

Structure 3

| $R^1$ | $R^2$ | $R^3$ | $R^4$ | $R^5$ | $R^6$ | Compound Double bond configuration as per drawing |
|---|---|---|---|---|---|---|
| H | H | H | H | $CH_3$ | $(CH_3)_2C{=}CHCH_2CH_2$ | 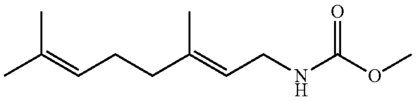 |
| H | H | $CH_3$ | H | $CH_3$ | $(CH_3)_2C{=}CHCH_2CH_2$ | 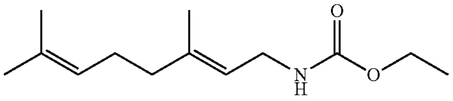 |
| H | H | $CH_3CH_2$ | H | $CH_3$ | $(CH_3)_2C{=}CHCH_2CH_2$ | 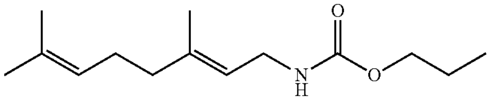 |
| H | H | $CH_3CH_2CH_2$ | H | $CH_3$ | $(CH_3)_2C{=}CHCH_2CH_2$ | 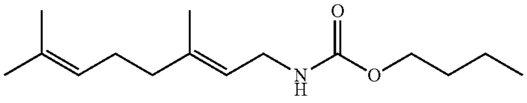 |
| H | $CH_3$ | $CH_3$ | H | $CH_3$ | $(CH_3)_2C{=}CHCH_2CH_2$ | 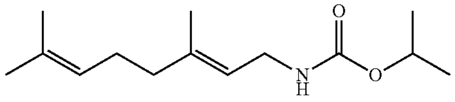 |
| H | H | $(CH_3)_3C$ | H | $CH_3$ | $(CH_3)_2C{=}CHCH_2CH_2$ | 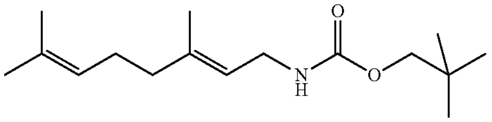 |
| H | $CH_3$ | $CH_3CH_2$ | H | $CH_3$ | $(CH_3)_2C{=}CHCH_2CH_2$ | 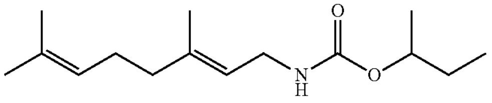 |

-continued

Structure 3

| $R^1$ | $R^2$ | $R^3$ | $R^4$ | $R^5$ | $R^6$ | Compound Double bond configuration as per drawing |
|---|---|---|---|---|---|---|
| H | H | 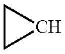 | H | $CH_3$ | $(CH_3)_2C{=}CHCH_2CH_2$ | 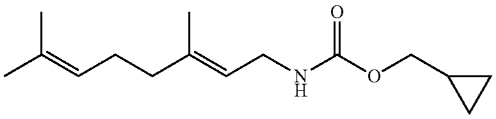 |
| | | 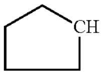 | H | $CH_3$ | $(CH_3)_2C{=}CHCH_2CH_2$ | 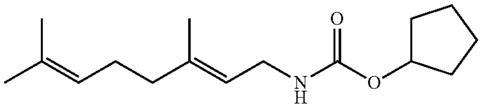 |
| | | 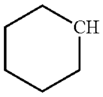 | H | $CH_3$ | $(CH_3)_2C{=}CHCH_2CH_2$ | 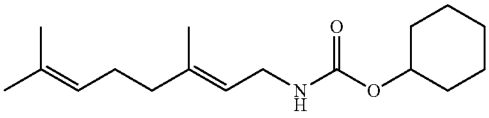 |
| | | 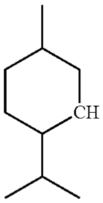 | H | $CH_3$ | $(CH_3)_2C{=}CHCH_2CH_2$ | 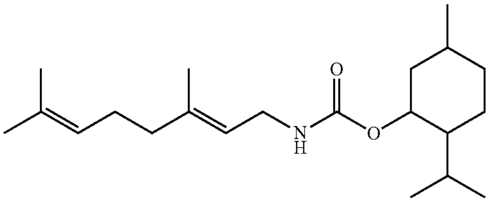 |
| H | | $CH_2$ | H | $CH_3$ | $(CH_3)_2C{=}CHCH_2CH_2$ | 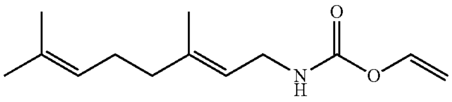 |
| H | H | $CH_2{=}CH$ | H | $CH_3$ | $(CH_3)_2C{=}CHCH_2CH_2$ | 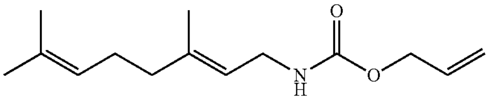 |
| $CH_3$ | | $CH_2$ | H | $CH_3$ | $(CH_3)_2C{=}CHCH_2CH_2$ | 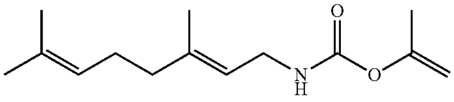 |
| H | H | $CH_2{=}CHCH_2$ | H | $CH_3$ | $(CH_3)_2C{=}CHCH_2CH_2$ | 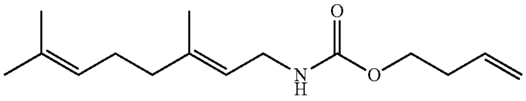 |
| H | H | $CH{\equiv}C$ | H | $CH_3$ | $(CH_3)_2C{=}CHCH_2CH_2$ | 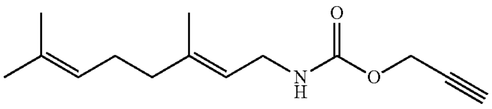 |
| H | H | $FCH_2$ | H | $CH_3$ | $(CH_3)_2C{=}CHCH_2CH_2$ | 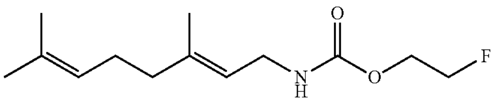 |
| H | H | $CH_3OCH_2$ | H | $CH_3$ | $(CH_3)_2C{=}CHCH_2CH_2$ | 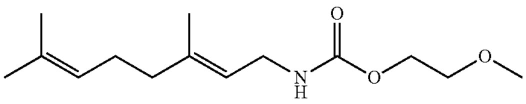 |
| H | H | $CH_3CH_2OCH_2$ | H | $CH_3$ | $(CH_3)_2C{=}CHCH_2CH_2$ | 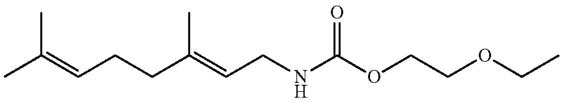 |

-continued

Structure 3

| $R^1$ | $R^2$ | $R^3$ | $R^4$ | $R^5$ | $R^6$ | Compound<br>Double bond configuration as per drawing |
|---|---|---|---|---|---|---|
| H | H | $CH_3OCH(CH_3)CH_2$ | H | $CH_3$ | $(CH_3)_2C{=}CHCH_2CH_2$ | 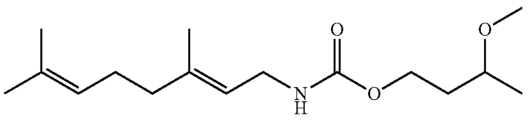 |
| H | H | $CH_3OC(CH_3)_2CH_2$ | H | $CH_3$ | $(CH_3)_2C{=}CHCH_2CH_2$ | 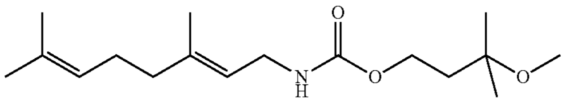 |
| | | 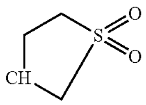 | H | $CH_3$ | $(CH_3)_2C{=}CHCH_2CH_2$ | 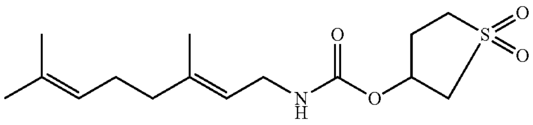 |
| H | H | 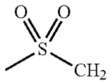 | H | $CH_3$ | $(CH_3)_2C{=}CHCH_2CH_2$ | 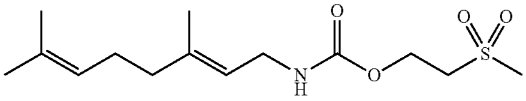 |
| H | H | 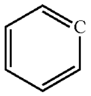 | H | $CH_3$ | $(CH_3)_2C{=}CHCH_2CH_2$ | 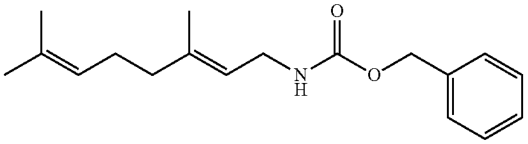 |
| | | 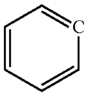 | H | $CH_3$ | $(CH_3)_2C{=}CHCH_2CH_2$ | 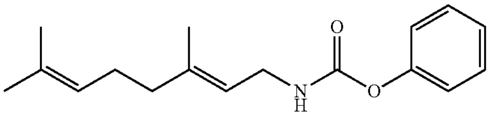 |
| | | 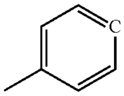 | H | $CH_3$ | $(CH_3)_2C{=}CHCH_2CH_2$ | 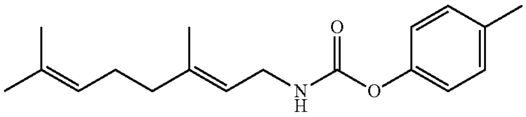 |
| | | 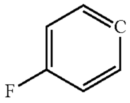 | H | $CH_3$ | $(CH_3)_2C{=}CHCH_2CH_2$ | 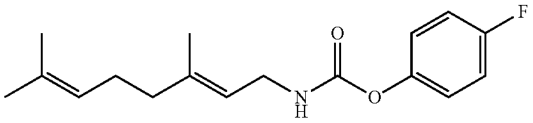 |
| | | 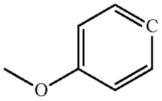 | H | $CH_3$ | $(CH_3)_2C{=}CHCH_2CH_2$ | 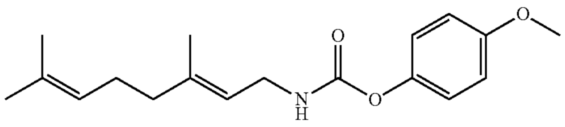 |
| | | 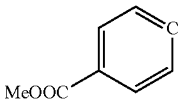 | H | $CH_3$ | $(CH_3)_2C{=}CHCH_2CH_2$ | 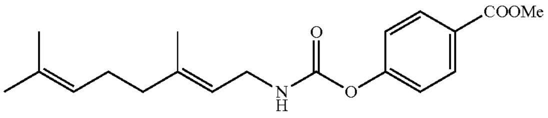 |
| H | H | H | H | $CH_3$ | $(CH_3)_2C{=}CHCH_2CH_2$ | 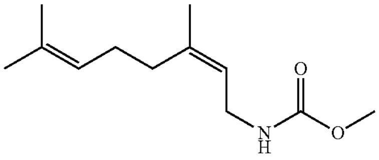 |

-continued
| Structure 3 | | | | | | |
|---|---|---|---|---|---|---|
| $R^1$ | $R^2$ | $R^3$ | $R^4$ | $R^5$ | $R^6$ | Compound<br>Double bond configuration as per drawing |
| H | H | $CH_3$ | H | $CH_3$ | $(CH_3)_2C{=}CHCH_2CH_2$ | 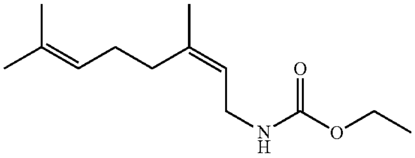 |
| H | H | $CH_3CH_2$ | H | $CH_3$ | $(CH_3)_2C{=}CHCH_2CH_2$ | 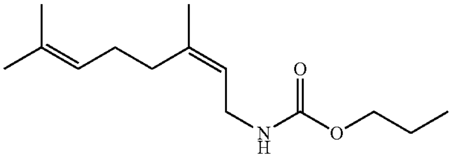 |
| H | H | $CH_3CH_2CH_2$ | H | $CH_3$ | $(CH_3)_2C{=}CHCH_2CH_2$ | 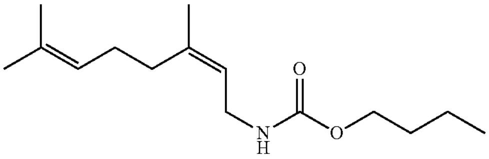 |
| H | $CH_3$ | $CH_3$ | H | $CH_3$ | $(CH_3)_2C{=}CHCH_2CH_2$ | 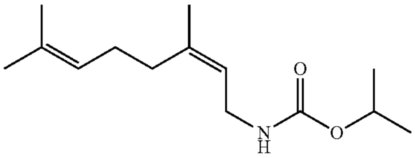 |
| H | H | $(CH_3)_3C$ | H | $CH_3$ | $(CH_3)_2C{=}CHCH_2CH_2$ | 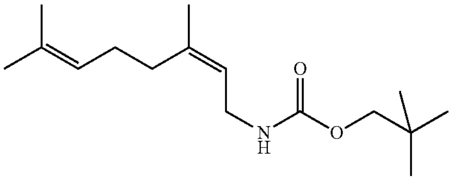 |
| H | $CH_3$ | $CH_3CH_2$ | H | $CH_3$ | $(CH_3)_2C{=}CHCH_2CH_2$ | 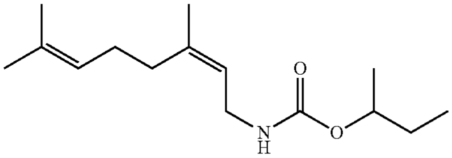 |
| H | H | 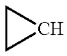 | H | $CH_3$ | $(CH_3)_2C{=}CHCH_2CH_2$ | 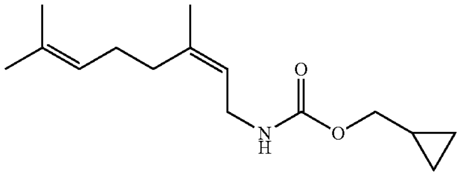 |
| | | 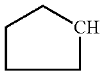 | H | $CH_3$ | $(CH_3)_2C{=}CHCH_2CH_2$ | 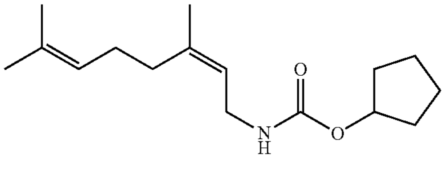 |

-continued
Structure 3
| $R^1$ | $R^2$ | $R^3$ | $R^4$ | $R^5$ | $R^6$ | Compound<br>Double bond configuration as per drawing |
|---|---|---|---|---|---|---|
| | | 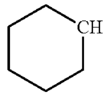 | H | $CH_3$ | $(CH_3)_2C{=}CHCH_2CH_2$ | 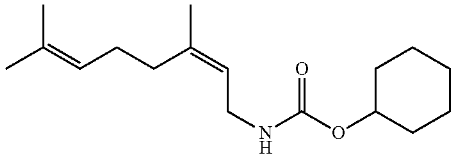 |
| | | 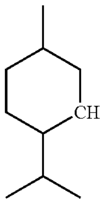 | H | $CH_3$ | $(CH_3)_2C{=}CHCH_2CH_2$ | 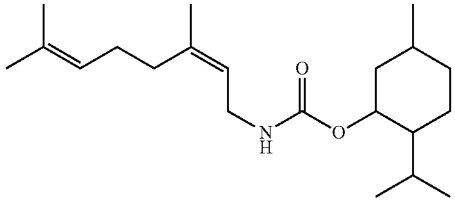 |
| H | | $CH_2$ | H | $CH_3$ | $(CH_3)_2C{=}CHCH_2CH_2$ | 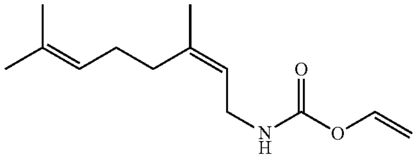 |
| H | H | $CH_2{=}CH$ | H | $CH_3$ | $(CH_3)_2C{=}CHCH_2CH_2$ | 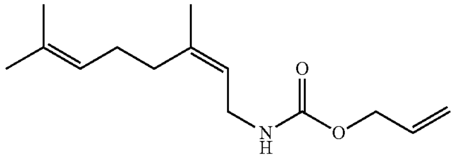 |
| $CH_3$ | | $CH_2$ | H | $CH_3$ | $(CH_3)_2C{=}CHCH_2CH_2$ | 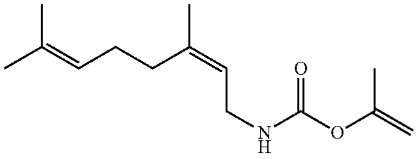 |
| H | H | $CH_2{=}CHCH_2$ | H | $CH_3$ | $(CH_3)_2C{=}CHCH_2CH_2$ | 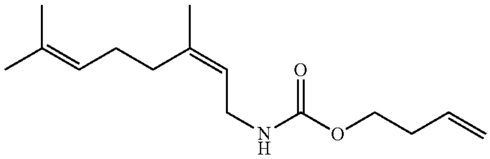 |
| H | H | $CH{\equiv}C$ | H | $CH_3$ | $(CH_3)_2C{=}CHCH_2CH_2$ | 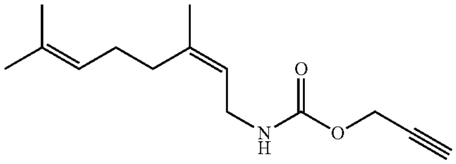 |
| H | H | $FCH_2$ | H | $CH_3$ | $(CH_3)_2C{=}CHCH_2CH_2$ | 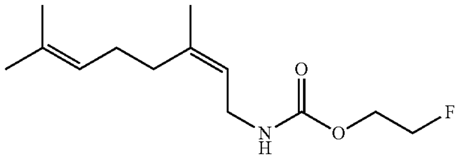 |

-continued
Structure 3
| $R^1$ | $R^2$ | $R^3$ | $R^4$ | $R^5$ | $R^6$ | Compound Double bond configuration as per drawing |
|---|---|---|---|---|---|---|
| H | H | $CH_3OCH_2$ | H | $CH_3$ | $(CH_3)_2C{=}CHCH_2CH_2$ | 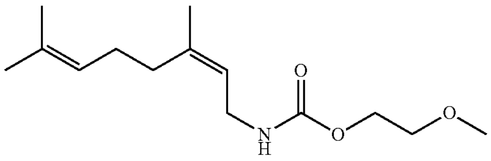 |
| H | H | $CH_3CH_2OCH_2$ | H | $CH_3$ | $(CH_3)_2C{=}CHCH_2CH_2$ | 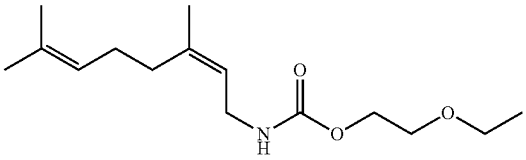 |
| H | H | $CH_3OCH(CH_3)CH_2$ | H | $CH_3$ | $(CH_3)_2C{=}CHCH_2CH_2$ | 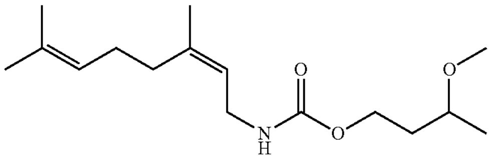 |
| H | H | $CH_3OC(CH_3)_2CH_2$ | H | $CH_3$ | $(CH_3)_2C{=}CHCH_2CH_2$ | 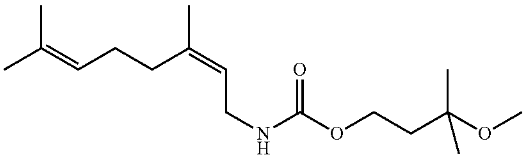 |
| | | 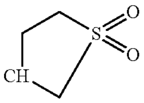 | H | $CH_3$ | $(CH_3)_2C{=}CHCH_2CH_2$ | 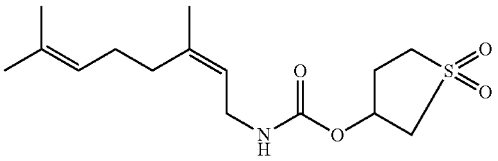 |
| H | H | 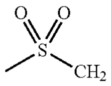 | H | $CH_3$ | $(CH_3)_2C{=}CHCH_2CH_2$ | 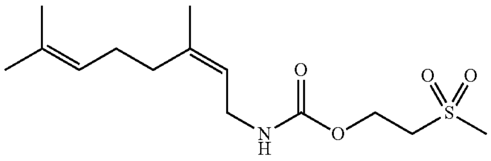 |
| H | H | 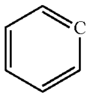 | H | $CH_3$ | $(CH_3)_2C{=}CHCH_2CH_2$ | 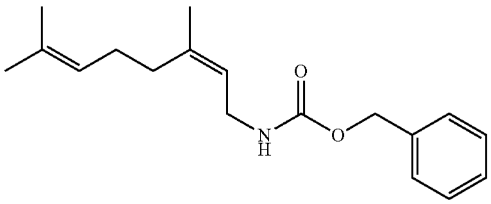 |
| | | 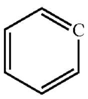 | H | $CH_3$ | $(CH_3)_2C{=}CHCH_2CH_2$ | 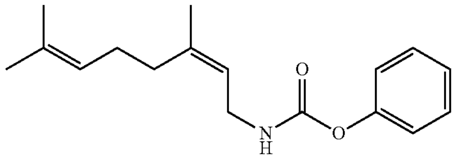 |

-continued

Structure 3

| $R^1$ | $R^2$ | $R^3$ | $R^4$ | $R^5$ | $R^6$ | Compound<br>Double bond configuration as per drawing |
|---|---|---|---|---|---|---|
| | | 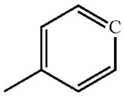 | H | $CH_3$ | $(CH_3)_2C{=}CHCH_2CH_2$ | 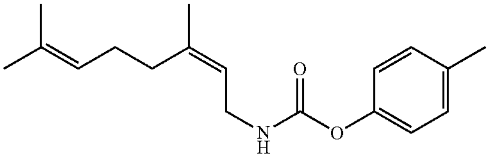 |
| | | 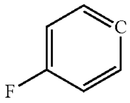 | H | $CH_3$ | $(CH_3)_2C{=}CHCH_2CH_2$ | 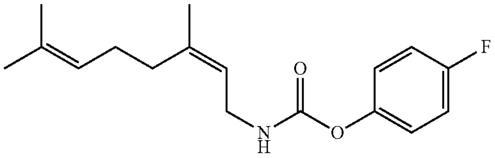 |
| | | 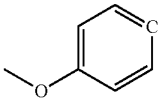 | H | $CH_3$ | $(CH_3)_2C{=}CHCH_2CH_2$ | 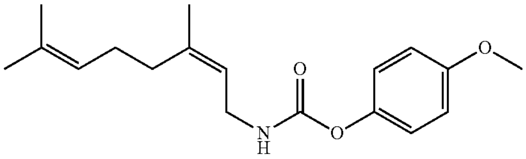 |
| | | 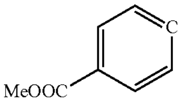 | H | $CH_3$ | $(CH_3)_2C{=}CHCH_2CH_2$ | 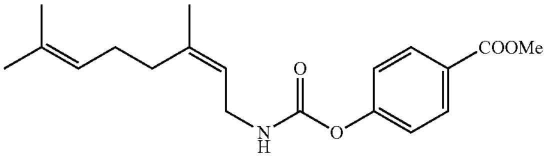 |
| H | H | H | H | H | $CH_3CH_2CH{=}CHCH_2CH_2$ | 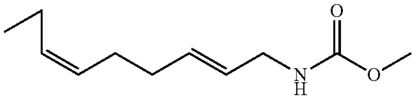 |
| H | H | $CH_3$ | H | H | $CH_3CH_2CH{=}CHCH_2CH_2$ | 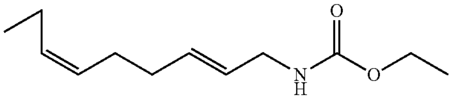 |
| H | H | $CH_3CH_2$ | H | H | $CH_3CH_2CH{=}CHCH_2CH_2$ | 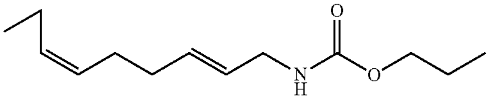 |
| H | H | $CH_3CH_2CH_2$ | H | H | $CH_3CH_2CH{=}CHCH_2CH_2$ | 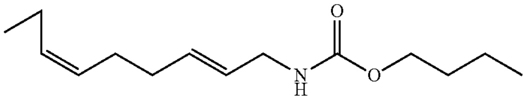 |
| H | $CH_3$ | $CH_3$ | H | H | $CH_3CH_2CH{=}CHCH_2CH_2$ | 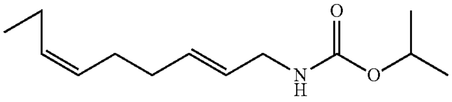 |
| H | H | $(CH_3)_3C$ | H | H | $CH_3CH_2CH{=}CHCH_2CH_2$ | 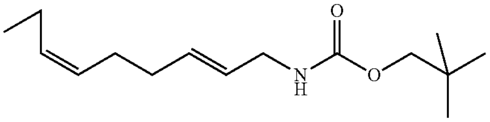 |
| H | $CH_3$ | $CH_3CH_2$ | H | H | $CH_3CH_2CH{=}CHCH_2CH_2$ | 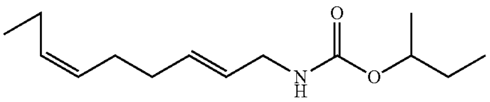 |

-continued

Structure 3

| $R^1$ | $R^2$ | $R^3$ | $R^4$ | $R^5$ | $R^6$ | Compound Double bond configuration as per drawing |
|---|---|---|---|---|---|---|
| H | H | 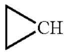 | H | H | $CH_3CH_2CH{=}CHCH_2CH_2$ | 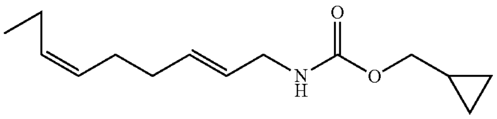 |
| | | 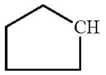 | H | H | $CH_3CH_2CH{=}CHCH_2CH_2$ | 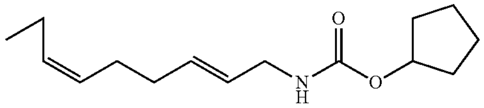 |
| | | 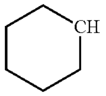 | H | H | $CH_3CH_2CH{=}CHCH_2CH_2$ | 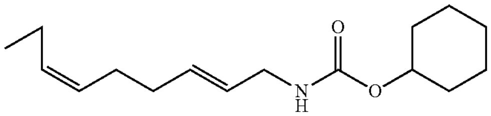 |
| | | 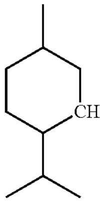 | H | H | $CH_3CH_2CH{=}CHCH_2CH_2$ | 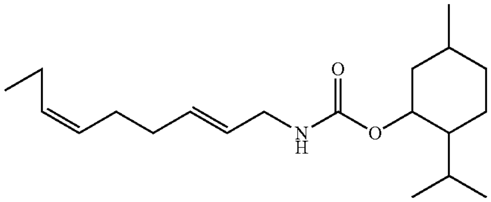 |
| H | | $CH_2$ | H | H | $CH_3CH_2CH{=}CHCH_2CH_2$ | 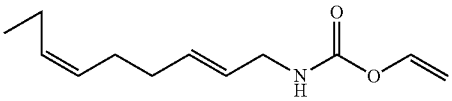 |
| H | H | $CH_2{=}CH$ | H | H | $CH_3CH_2CH{=}CHCH_2CH_2$ | 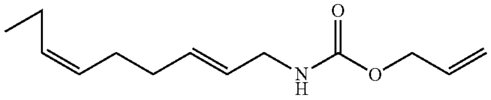 |
| $CH_3$ | | $CH_2$ | H | H | $CH_3CH_2CH{=}CHCH_2CH_2$ | 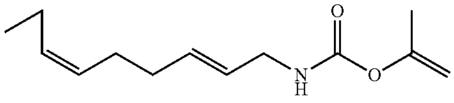 |
| H | H | $CH_2{=}CHCH_2$ | H | H | $CH_3CH_2CH{=}CHCH_2CH_2$ | 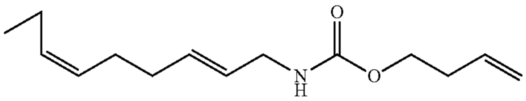 |
| H | H | $CH{\equiv}C$ | H | H | $CH_3CH_2CH{=}CHCH_2CH_2$ | 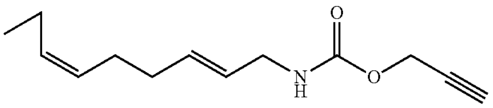 |
| H | H | $FCH_2$ | H | H | $CH_3CH_2CH{=}CHCH_2CH_2$ | 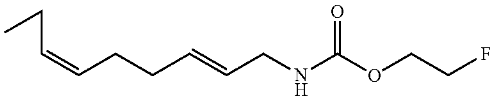 |
| H | H | $CH_3OCH_2$ | H | H | $CH_3CH_2CH{=}CHCH_2CH_2$ | 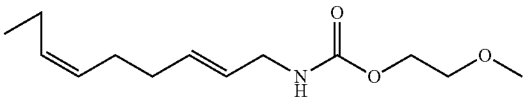 |
| H | H | $CH_3CH_2OCH_2$ | H | H | $CH_3CH_2CH{=}CHCH_2CH_2$ | 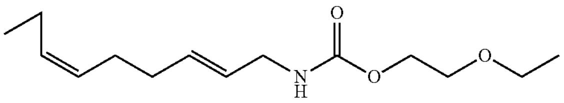 |

-continued
| Structure 3 | | | | | | |
|---|---|---|---|---|---|---|
| $R^1$ | $R^2$ | $R^3$ | $R^4$ | $R^5$ | $R^6$ | Compound Double bond configuration as per drawing |
| H | H | $CH_3OCH(CH_3)CH_2$ | H | H | $CH_3CH_2CH{=}CHCH_2CH_2$ | 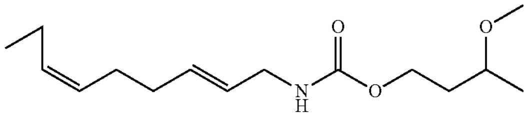 |
| H | H | $CH_3OC(CH_3)_2CH_2$ | H | H | $CH_3CH_2CH{=}CHCH_2CH_2$ | 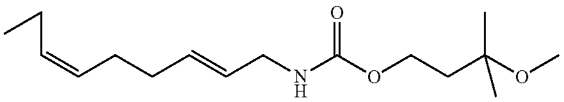 |
| | | 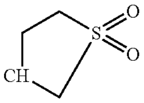 | H | H | $CH_3CH_2CH{=}CHCH_2CH_2$ | 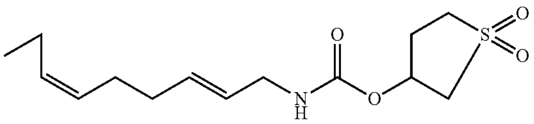 |
| H | H | 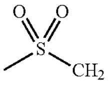 | H | H | $CH_3CH_2CH{=}CHCH_2CH_2$ | 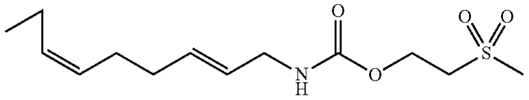 |
| H | H | 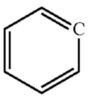 | H | H | $CH_3CH_2CH{=}CHCH_2CH_2$ | 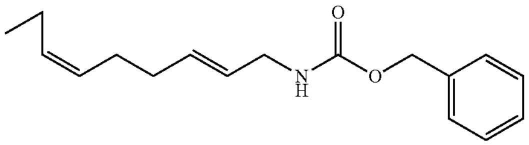 |
| | | 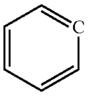 | H | H | $CH_3CH_2CH{=}CHCH_2CH_2$ | 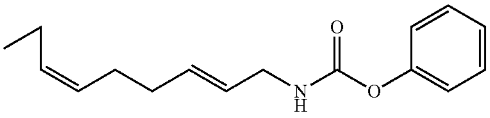 |
| | | 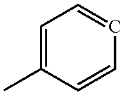 | H | H | $CH_3CH_2CH{=}CHCH_2CH_2$ | 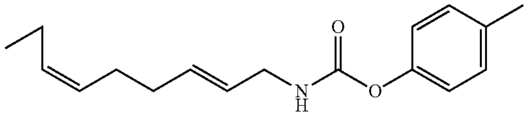 |
| | | 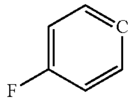 | H | H | $CH_3CH_2CH{=}CHCH_2CH_2$ | 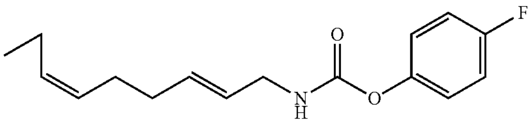 |
| | | 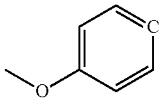 | H | H | $CH_3CH_2CH{=}CHCH_2CH_2$ | 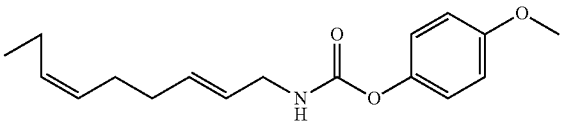 |
| | | 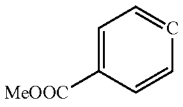 | H | H | $CH_3CH_2CH{=}CHCH_2CH_2$ | 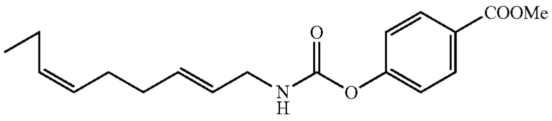 |
| H | H | H | H | H | 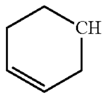 | 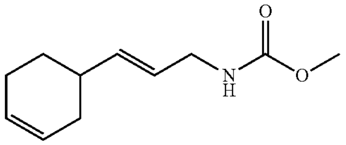 |

-continued
Structure 3
| $R^1$ | $R^2$ | $R^3$ | $R^4$ | $R^5$ | $R^6$ | Compound Double bond configuration as per drawing |
|---|---|---|---|---|---|---|
| H | H | $CH_3$ | H | H | 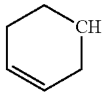 | 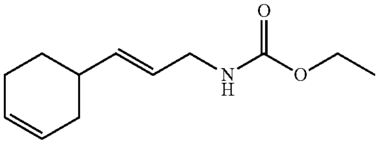 |
| H | H | $CH_3CH_2$ | H | H | 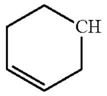 | 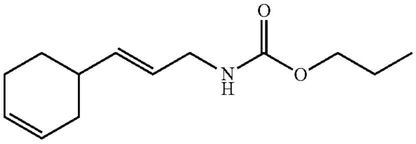 |
| H | H | $CH_3CH_2CH_2$ | H | H | 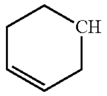 | 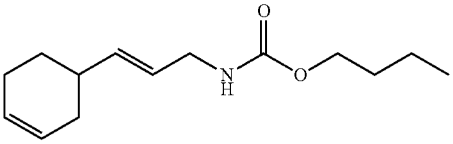 |
| H | $CH_3$ | $CH_3$ | H | H | 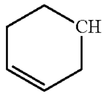 | 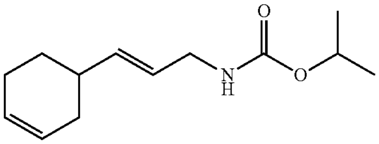 |
| H | H | $(CH_3)_3C$ | H | H | 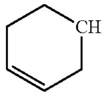 | 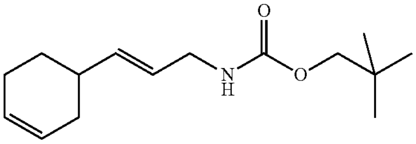 |
| H | $CH_3$ | $CH_3CH_2$ | H | H | 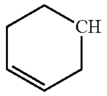 | 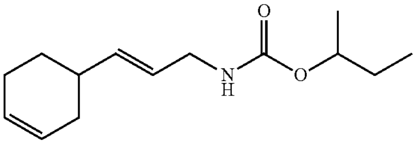 |
| H | H | 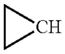 | H | H | 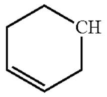 | 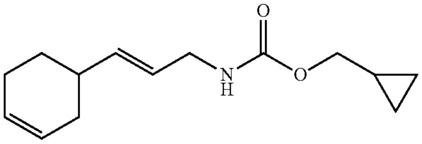 |
| | | 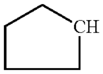 | H | H | 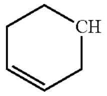 | 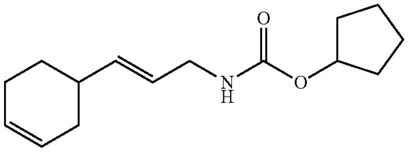 |
| | | 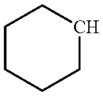 | H | H | 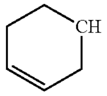 | 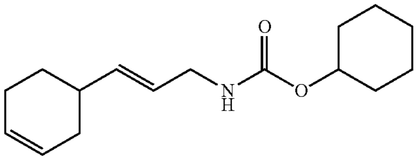 |

-continued
Structure 3
| $R^1$ | $R^2$ | $R^3$ | $R^4$ | $R^5$ | $R^6$ | Compound<br>Double bond configuration as per drawing |
|---|---|---|---|---|---|---|
| | | 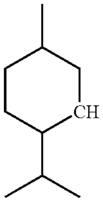 | H | H | 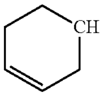 | 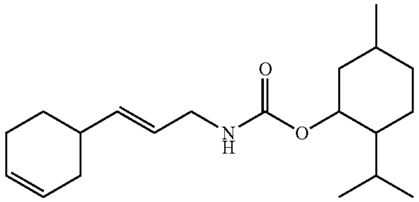 |
| H | | $CH_2$ | H | H | 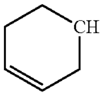 | 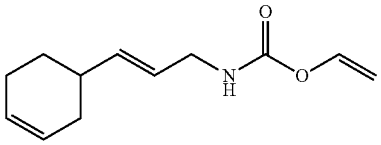 |
| H | H | $CH_2{=}CH$ | H | H | 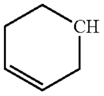 | 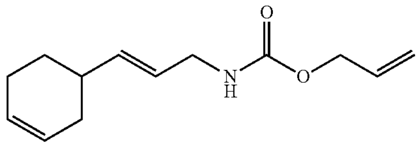 |
| $CH_3$ | | $CH_2$ | H | H | 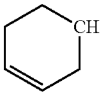 | 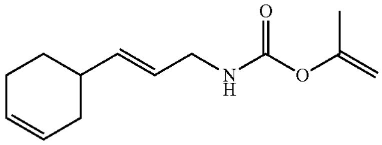 |
| H | H | $CH_2{=}CHCH_2$ | H | H | 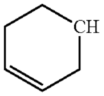 | 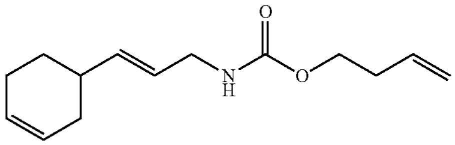 |
| H | H | $CH{\equiv}C$ | H | H | 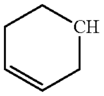 | 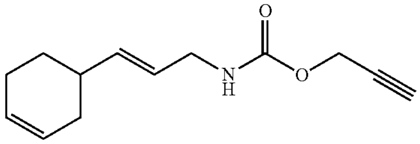 |
| H | H | $FCH_2$ | H | H | 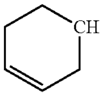 | 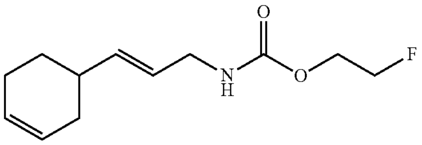 |
| H | H | $CH_3OCH_2$ | H | H | 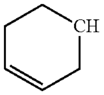 | 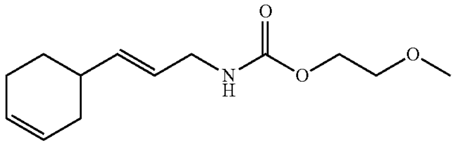 |
| H | H | $CH_3CH_2OCH_2$ | H | H | 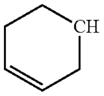 | 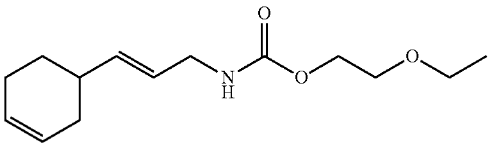 |

-continued
Structure 3
| $R^1$ | $R^2$ | $R^3$ | $R^4$ | $R^5$ | $R^6$ | Compound Double bond configuration as per drawing |
|---|---|---|---|---|---|---|
| H | H | $CH_3OCH(CH_3)CH_2$ | H | H | 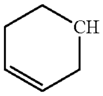 | 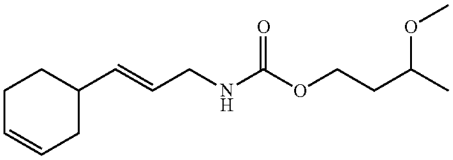 |
| H | H | $CH_3OC(CH_3)_2CH_2$ | H | H | 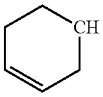 | 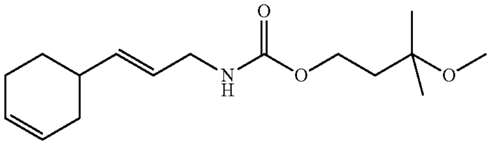 |
| | | 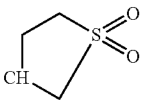 | H | H | 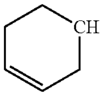 | 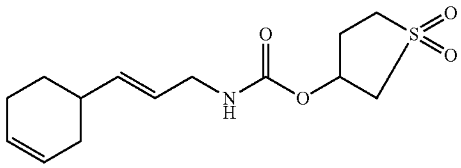 |
| H | H | 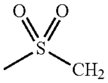 | H | H | 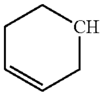 | 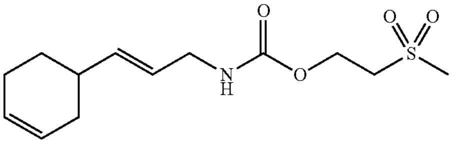 |
| H | H | 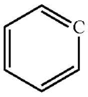 | H | H | 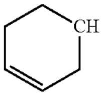 | 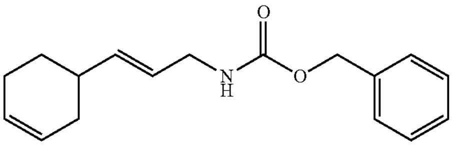 |
| | | 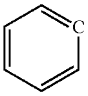 | H | H | 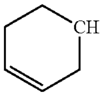 | 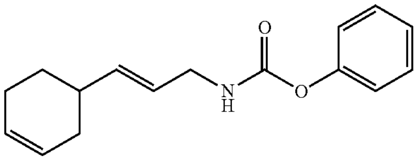 |
| | | 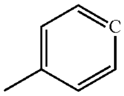 | H | H | 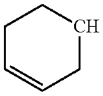 | 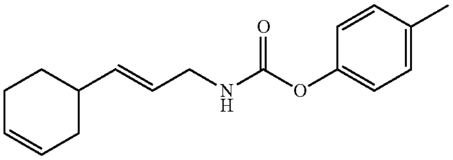 |
| | | 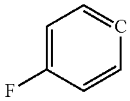 | H | H | 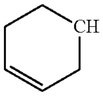 | 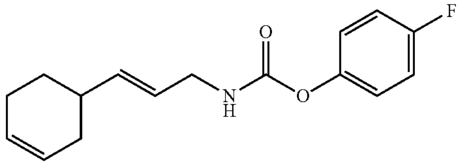 |
| | | 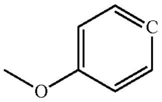 | H | H | 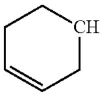 | 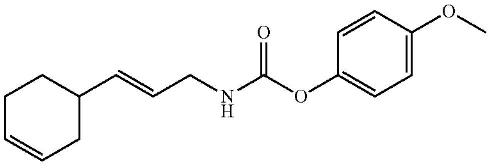 |

-continued
Structure 3
| $R^1$ | $R^2$ | $R^3$ | $R^4$ | $R^5$ | $R^6$ | Compound Double bond configuration as per drawing |
|---|---|---|---|---|---|---|
| | | 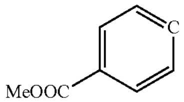 | H | H | 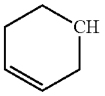 | 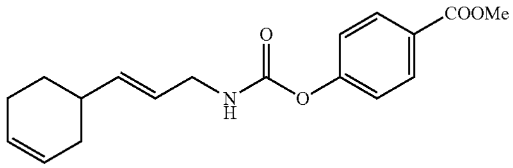 |
| H | H | H | | | 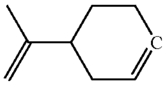 | 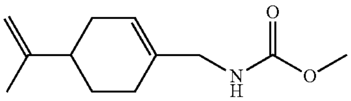 |
| H | H | $CH_3$ | | | 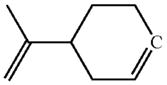 | 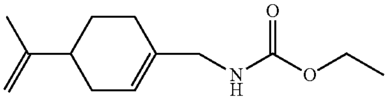 |
| H | H | $CH_3CH_2$ | | | 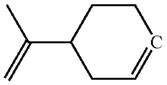 | 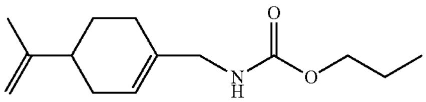 |
| H | H | $CH_3CH_2CH_2$ | | | 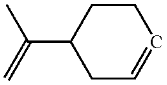 | 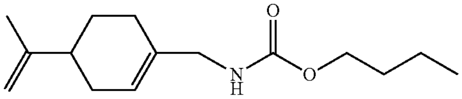 |
| H | $CH_3$ | $CH_3$ | | | 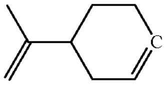 | 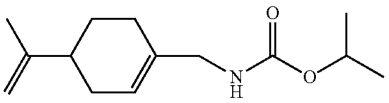 |
| H | H | $(CH_3)_3C$ | | | 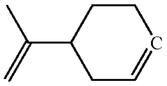 | 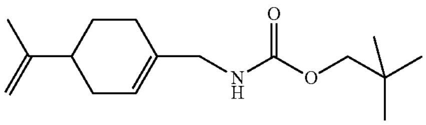 |
| H | $CH_3$ | $CH_3CH_2$ | | | 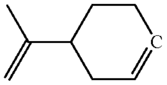 | 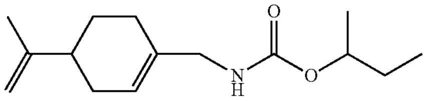 |
| H | H | 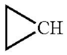 | | | 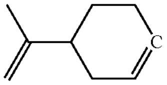 | 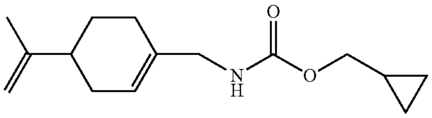 |
| | | 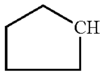 | | | 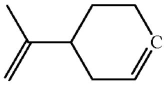 | 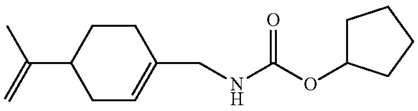 |
| | | 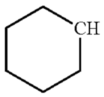 | | | 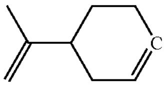 | 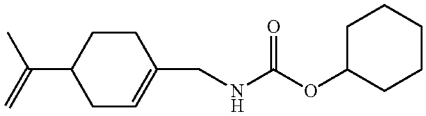 |

-continued
| Structure 3 | | | | | | |
|---|---|---|---|---|---|---|
| $R^1$ | $R^2$ | $R^3$ | $R^4$ | $R^5$ | $R^6$ | Compound<br>Double bond configuration as per drawing |
| | | 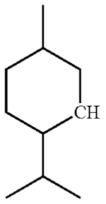 | | | 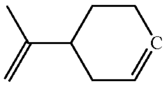 | 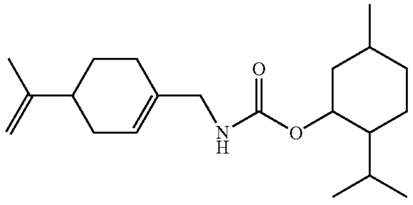 |
| H | | $CH_2$ | | | 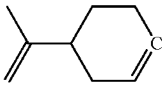 | 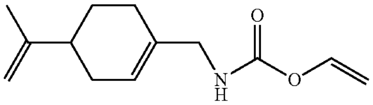 |
| H | H | $CH_2{=}CH$ | | | 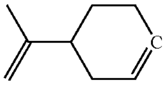 | 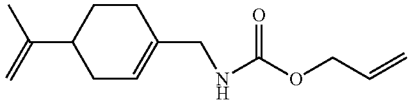 |
| $CH_3$ | | $CH_2$ | | | 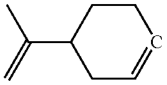 | 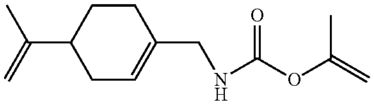 |
| H | H | $CH_2{=}CHCH_2$ | | | 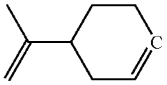 | 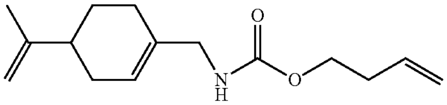 |
| H | H | $CH{\equiv}C$ | | | 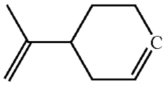 | 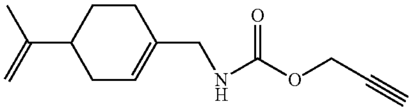 |
| H | H | $FCH_2$ | | | 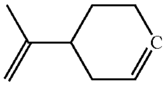 | 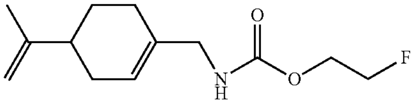 |
| H | H | $CH_3OCH_2$ | | | 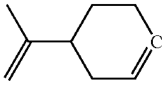 | 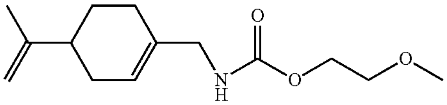 |
| H | H | $CH_3CH_2OCH_2$ | | | 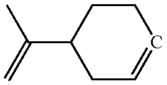 | 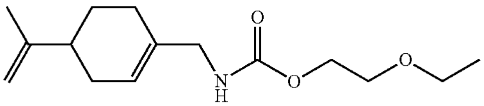 |
| H | H | $CH_3OCH(CH_3)CH_2$ | | | 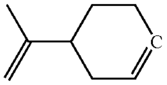 | 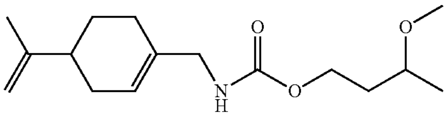 |
| H | H | $CH_3OC(CH_3)_2CH_2$ | | | 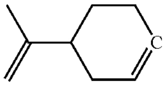 | 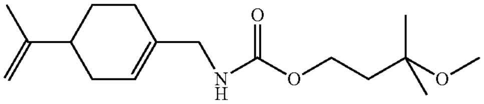 |

-continued

Structure 3

| R[1] | R[2] | R[3] | R[4] | R[5] | R[6] | Compound Double bond configuration as per drawing |
|---|---|---|---|---|---|---|
| | | 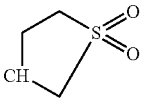 | | | 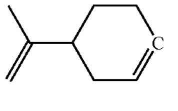 | 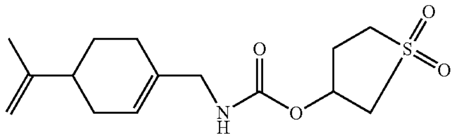 |
| H | H | 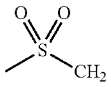 | | | 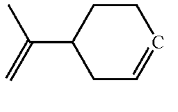 | 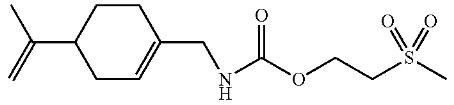 |
| H | H | 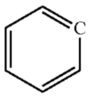 | | | 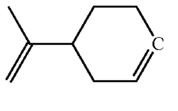 | 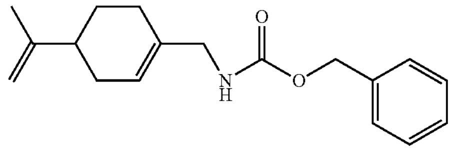 |
| | | 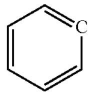 | | | 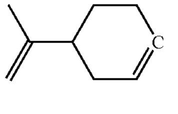 | 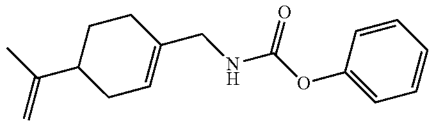 |
| | | 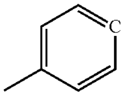 | | | 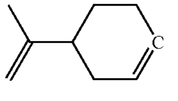 | 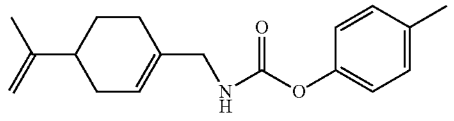 |
| | | 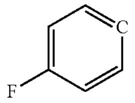 | | | 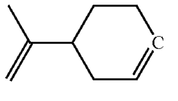 | 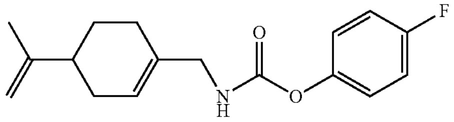 |
| | | 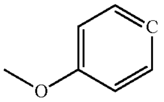 | | | 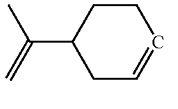 | 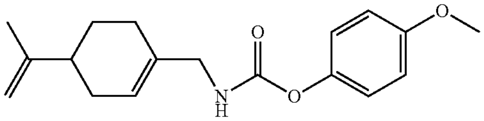 |
| | | 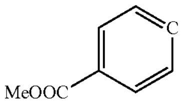 | | | 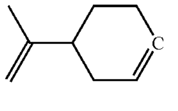 | 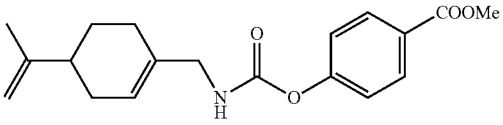 |

We have surprisingly found the literature has not previously reported unsaturated cyclic and acyclic carbamates as having or enhancing umami flavor. In addition, closely structurally related compounds such as dienals and alcohols are not specifically reported to possess umami character when tasted in isolation. In addition the ability to provide an enhanced saltiness for the product without increasing sodium level is not disclosed or suggested by the prior art. The salt enhancing properties of the compounds of the present invention are important because it allows flavorists to provide the desired salty taste profile in foods and beverages without actually having higher salt levels in the food. Therefore the consumer can have both the taste profile that they desire while without having the adverse health effects associated with increased salt levels such as hypertension.

As used herein olfactory effective amount is understood to mean the amount of compound in flavor compositions the individual component will contribute to its particular olfactory characteristics, but the flavor, taste and aroma effect on the overall composition will be the sum of the effects of each of the flavor ingredients. As used herein taste effects include salt, sweet and umami effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of carbamates used in products is greater than 50 parts per billion, generally provided at a level of from about 0.01 parts per million to about 50 parts per million in the finished product, more preferably from about 0.1 parts per million to about 20 parts per million by weight, and in preferred embodiments from about 0.5 to about 5 parts per million.

The usage level of carbamates varies depending on the product in which the carbamates are employed. For example, alcoholic beverages the usage level is from about 0.1 to about 5 parts per million, preferably from about 0.5 to about 3 and most preferably from about 1 to about 2 parts per million by weight. Non-alcoholic beverages are flavored at levels of from about 0.05 parts per million to about 5 parts per million, preferably from about 0.1 parts per billion to about 2 parts per million and in highly preferred situations of from about 0.7 to about 1 part per billion. Other products such as snack foods, candy and gum products can be advantageously flavored using compounds of the present invention at levels described above.

Among the preferred compounds of the present invention are:

N-[(2E)-3,7-Dimethyl-2,6-octadienyl]-carbamic acid, ethyl ester;

N-[(2E)-3,7-Dimethyl-2,6-octadienyl]-carbamic acid, isopropyl ester;

N-[(2E)-3,7-Dimethyl-2,6-octadienyl]-carbamic acid, allyl ester;

N-[(2Z)-3,7-Dimethyl-2,6-octadienyl]-carbamic acid, ethyl ester;

N-[(2E,6Z)-2,6-Nonadienyl]-carbamic acid, ethyl ester;

N-[(2E)-3-(3-cyclohexen-1-yl)-2-propenyl]-carbamic acid, ethyl ester;

N-[[4-(1-Methylethenyl)-1-cyclohexen-1-yl]methyl]-carbamic acid, ethyl ester.

The present invention also provides a method for enhancing or modifying the salt flavor of a food through the incorporation of an organoleptically acceptable level of the compounds described herein. The compounds can be used individually or in combination with other salt enhancing compounds of the present invention. In addition, the salt enhancing materials of the present invention can be used in combination with other salt enhancing compositions known in the art, including those materials listed in applications U.S. Ser. No. 10/919,631 filed on Aug. 17, 2004, now U.S. Pat. No. 7,329,767; U.S. Ser. No. 10/861,751 filed on Jun. 4, 2004, now U.S. Pat. No. 7,098,350; and U.S. Ser. No. 10/783,652 filed Feb. 20, 2004, now U.S. Pat. No. 7,632,531; and also include cetylpyridium chloride, bretylium tosylate, various polypeptides, mixtures of calcium salts of ascorbic acid, sodium chloride and potassium chloride, as described in various U.S. Pat. Nos. 4,997,672; 5,288,510; 6,541,050 and U.S. Patent Application Publication No. 2003/0091721.

The salt taste enhancing compounds of the present invention may be employed to enhance the perceived salt taste of any salts used in food or beverage products. The preferred salt taste to be enhanced by the compounds of the present invention is that of sodium chloride, primarily because of the discovery that ingestion of large amounts of sodium may have adverse effects on humans and the resultant desirability of reducing salt content while retaining salt taste.

In addition, the compounds of the present invention may also be employed to enhance the perceived salt taste of known salty tasting compounds which may be used as salt substitutes, including potassium chloride and ribonucleotides. Suitable compounds also include cationic amino acids and low molecular weight dipeptides. Specific examples of these compounds are arginine hydrochloride, arginine ammonium chloride, lysine hydrochloride and lysine-ornithine hydrochloride. These compounds exhibit a salty taste but are typically useful only at low concentrations since they exhibit a bitter flavor at higher concentrations. Thus, it is feasible to reduce the sodium chloride content of a food or beverage product by first formulating a food or beverage with less sodium chloride than is necessary to achieve a desired salt taste and then adding to said food or beverage the compounds of the present invention in an amount sufficient to potentiate the salt taste of said salted food or beverage to reach said desired taste. In addition, the sodium chloride content may be further reduced by substituting a salty-tasting cationic amino acid, a low molecular weight dipeptide or mixtures thereof for at least a portion of the salt.

In a preferred embodiment of the present invention we have found the compound of the present invention are materials used in combination with each other or other salt enhancing materials in weight ratios of from about 1:10 to about 10:1, typically from about 1:3 to about 3:1; more preferably from about 1:1 on a weight basis.

In a highly preferred embodiment we have discovered that the compounds of the present invention when used in combination with the compounds disclosed in applications U.S. Ser. No. 10/783,652 filed Feb. 20, 2004, now U.S. Pat. No. 7,632,531 and U.S. patent application Ser. No. 11/178,179 filed Jul. 8, 2005, now U.S. Pat. No. 7,541,055.

The preferred compounds disclosed in this application include but are not limited to:

The mixtures of the compounds range from about 1:10 to 10:1 weight percent, preferably from about 1:5 to about 5:1 weight percent, most preferably in a 1:2 to a 2:1 weight ratio of the compounds with a total use level of 8 ppm. For purpose of illustration that would be a usage level of about 4, 2 and 2 parts per million respectively by weight in a product such as a foodstuff.

The term "foodstuff" as used herein includes both solid and liquid ingestible materials for man or animals, which materials usually do, but need not, have nutritional value. Thus, foodstuffs include food products, such as, meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the compounds of our invention; (2) that they be organoleptically compatible with the compounds of our invention whereby the flavor of the ultimate consumable material to which the compounds are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the dienalkylamides of our invention and aldehydes; lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

The carbamates of our invention or compositions incorporating them, as mentioned above, can be combined with one or more vehicles or carriers for adding them to the particular product. Vehicles can be edible or otherwise suitable materials such as ethyl alcohol, propylene glycol, water and the like, as described above. Carriers include materials such as gum arabic, carrageenan, xanthan gum, guar gum and the like.

The cyclic and acyclic unsaturated carbamates prepared according to our invention can be incorporated with the carriers by conventional means such as spray-drying, extrusion, drum-drying and the like. Such carriers can also include materials for coacervating the carbamates of our invention to provide encapsulated products, as set forth above. When the carrier is an emulsion, the flavoring composition can also contain emulsifiers such as mono- and diglycerides or fatty acids and the like. With these carriers or vehicles, the desired physical form of the compositions can be prepared.

The quantity of carbamates utilized should be sufficient to impart the desired flavor characteristic to the product, but on the other hand, the use of an excessive amount of the compounds is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology "organoleptically effective amount" and "sufficient amount" is understood in the context of the present invention to be quantitatively adequate to alter the flavor of the foodstuff.

The carbamates of the present invention can be admixed with other flavoring agents and incorporated into foodstuffs and other products using techniques well known to those with ordinary skill in the art. Most commonly the carbamates are simply admixed using the desired ingredients within the proportions stated.

With reference to the novel compounds of our invention, the synthesis is effected by means of the reaction of a chloroformate with an amine, added either directly or in solution, according to the general scheme:

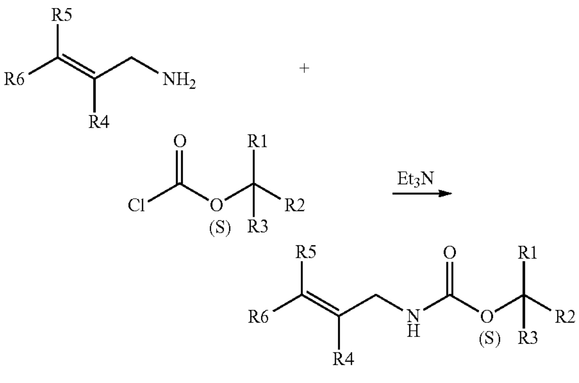

where $R^1$, $R^2$, $R^3$, $R^4$, $R^5$ and $R^6$ have the meaning set forth in Structures 1 and 2 above.

The synthesis of amine follows a literature procedure as recited in The Journal of Organic Chemistry 1989, 54, 3292-3303. The amine and triethylamine are dissolved in dichloromethane or ethyl acetate to which the corresponding chloroformate is added in 1.0 to 2.0 equivalents at temperatures ranging 0° C. to room temperature, most preferably from 5° C. to 15° C. The resulting solution is aged for about 1-3 hours at room temperature.

The reaction can be quenched with aqueous sodium chloride, hydrogen chloride or sodium hydroxide depending upon the need to remove residual acid or amine. The mixture is extracted into ethereal solvent, washed to neutrality and solvent removed.

The crude product is purified by distillation or recrystallization depending on the physical properties. The reaction occurs in 35-70% mole yield based on amine.

The following are provided as specific embodiments of the present invention. Other modifications of this invention will be readily apparent to those skilled in the art, without departing from the scope of this invention. As used herein, in both the specification and following examples, all percentages are understood to be molar percent unless noted to the contrary.

All U.S. Patents and U.S. Patent Applications cited herein are incorporated by reference as if set forth in their entirety. Upon review of the foregoing, numerous adaptations, modifications, and alterations will occur to the reviewer. These will all be, however, within the spirit of the present invention. Accordingly, reference should be made to the appended claims in order to ascertain the true scope of the present invention.

Example 1

Preparation of Materials of the Present Invention

The following reaction sequence was used to prepare the specific compounds described by the NMR data set forth below:

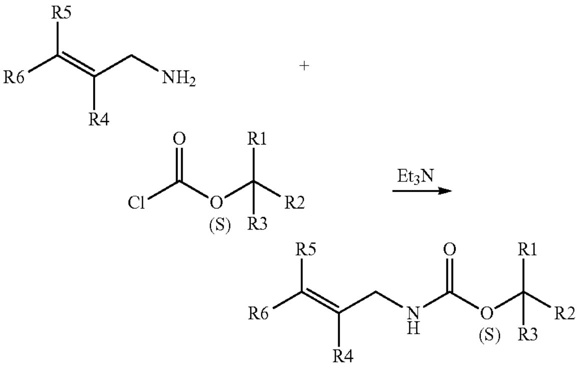

The amine and triethylamine were dissolved in dichloromethane or ethyl acetate to which the corresponding chloroformate was added in 1.0 to 2.0 equivalents at temperatures ranging from 0° C. to room temperature, most preferably from 5° C. to 15° C. The resulting solution was aged for about 1-3 hours at room temperature.

The reaction was quenched with aqueous sodium chloride, hydrogen chloride or sodium hydroxide depending upon the need to remove residual acid or amine. The mixture was extracted into ethereal solvent or dichloromethane, washed to neutrality and solvent removed.

The crude product was purified by distillation or recrystallization depending on the physical properties.

The carbamates were synthesized according to the general scheme above with the following specific examples. Equivalents set out were mole equivalents based on starting amine, yields were purified chemical yields based on starting amine.

N-[(2E)-3,7-Dimethyl-2,6-octadienyl]-carbamic acid, ethyl ester

Ethyl chloroformate 1.2 eq, 3,7-dimethylocta-2E,6-dienylamine 1.0 eq, triethylamine 1.5 eq, quench with 10% sodium chloride solution, yield=31%.

1.24-1.25 ppm (m, 3H), 1.60-1.71 ppm (m, 9H), 1.99-2.02 ppm (m, 2H), 2.06-2.09 ppm (m, 2H), 3.77 ppm (s, 2H), 4.10-4.12 ppm (m, 2H), 4.66-4.70 ppm (m, 1H), 5.07-5.09 ppm (m, 1H), 5.20-5.21 ppm (m, 1H).

N-[(2Z)-3,7-Dimethyl-2,6-octadienyl]-carbamic acid, ethyl ester

Ethyl chloroformate 1.2 eq, 3,7-dimethylocta-2Z,6-dienylamine 1.0 eq, triethylamine 1.5 eq, quench with 10% sodium chloride solution, yield=72%.

1.23 ppm (br. s, 3H), 1.60-1.72 ppm (m, 9H), 1.96-2.29 ppm (m, 4H), 3.74 ppm (m, 2H), 4.11 ppm (br. s, 2H), 4.62 ppm (br. s, 1H), 5.09 ppm (s, 1H), 5.17-5.22 ppm (m, 1H).

N-[(2E)-3,7-Dimethyl-2,6-octadienyl]-thiocarbamic acid, ethyl ester

Ethyl chlorothioformate 1.1 eq, 3,7-dimethylocta-2E,6-dienylamine 1.0 eq, triethylamine 1.3 eq, quench with 10% sodium chloride solution, yield=7%.

1.29 ppm (t, 3H, J=7.3 Hz, of d, J=2.4 Hz), 1.60 ppm (s, 3H), 1.63-1.72 ppm (m, 6H), 1.98-2.09 ppm (m, 4H), 2.89-2.94 ppm (q, 2H, J=7.3 Hz, of d, J=2.5 Hz), 3.89 ppm (s, 2H), 5.06-5.08 ppm (m, 1H), 5.19-5.22 ppm (m, 1H), 5.28 ppm (br. s, 1H).

N-[(2E)-3,7-Dimethyl-2,6-octadienyl]-carbamic acid, methyl ester

Methyl chloroformate 1.2 eq, 3,7-dimethylocta-2E,6-dienylamine 1.0 eq, triethylamine 1.5 eq, quench with 10% sodium chloride solution, yield=47%.

1.60 ppm (s, 3H), 1.66-1.71 ppm (m, 6H), 1.96-2.02 ppm, (m, 2H), 2.07-2.17 ppm (m, 2H), 3.67-3.78 ppm (m, 5H), 4.66-4.70 ppm (m, 1H), 5.06-5.09 ppm (m, 1H), 5.18-5.21 ppm (m, 1H).

N-[(2E)-3,7-Dimethyl-2,6-octadienyl]-carbamic acid, 2-propenyl ester

Allyl chloroformate 1.2 eq, 3,7-dimethylocta-2E,6-dienylamine 1.0 eq, triethylamine 1.5 eq, quench with 10% sodium chloride solution, yield=63%.

1.60 ppm (s, 3H), 1.66 ppm (s, 3H), 1.68 ppm (s, 3H), 1.96-2.04 ppm (m, 2H), 2.05-2.13 ppm (m, 2H), 3.79 ppm (s, 2H), 4.57 ppm (s, 2H), 4.66-4.70 ppm (m, 1H), 5.07 ppm (m, 1H), 5.19-5.26 ppm (m, 2H), 5.30 ppm (m, 1H), 5.89-5.95 ppm (m, 1H).

N-[[4-(1-Methylethenyl)-1-cyclohexen-1-yl]methyl]-carbamic acid, ethyl ester

[4-(1-Methylethenyl)-1-cyclohexen-1-yl]methylamine was synthesized following a reported procedure. [Synthesis, 1995, 756-758]

Ethyl chloroformate 1.1 eq, [4-(1-methylethenyl)-1-cyclohexen-1-yl]methylamine 1.0 eq, triethylamine 1.3 eq, quench with 10% sodium chloride solution, yield=37%.

1.24 ppm (t, 3H, J=7.0 Hz), 1.45-1.49 ppm (m, 1H), 1.65-1.69 ppm (m, 1H), 1.73 ppm (s, 3H), 1.81-2.15 ppm (m, 5H), 3.69 ppm (s, 2H), 4.12 ppm (q, 2H, J=6.8 Hz), 4.70-4.72 ppm (m, 3H), 5.59 ppm (m, 1H).

N-[(2E)-3,7-Dimethyl-2,6-octadienyl]-carbamic acid, ethenyl ester

Vinyl chloroformate 1.1 eq, 3,7-dimethylocta-2E,6-dienylamine 1.0 eq, triethylamine 1.3 eq, quench with 10% sodium chloride solution, yield=93%.

1.60 ppm (s, 3H), 1.68 ppm (s, 6H), 1.96-2.05 ppm (m, 2H), 2.05-2.13 ppm (m, 2H), 3.80-3.82 ppm (m, 2H), 4.40 ppm (d, 1H, J=5.8 Hz), 4.70 ppm (d, 1H, J=13.9 Hz), 4.83 ppm (br. s, 1H), 5.07 ppm (t, 1H, J=6.4 Hz), 5.21 ppm (t, 1H, J=6.1 Hz), 7.21 ppm (d, 1H, J=13.9 Hz, of d, J=6.2 Hz).

Example II

The following reaction sequence was used to make the compound described by the NMR data set forth below:

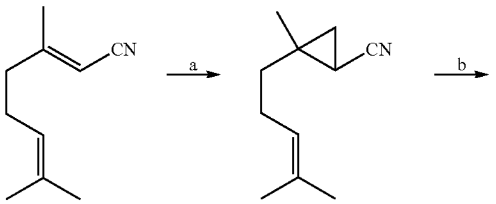

I II

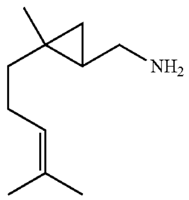

III a) $Me_3SOI$, NaH, DMSO
b) $LiAlH_4$, IPA

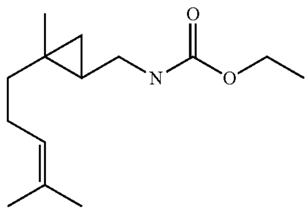

Corey's cyclopropanation of compound I, a chemical that is commercially known as Citralva, gives rise to compound II in good yield. The above mentioned transformation proceeds via the trimethylsulfoxium ylide which is generated in-situ from the reaction of trimethylsulfoxium iodide, $(CH_3)_3SOI$, and sodium hydride in dimethylsulfoxide, DMSO. Next, metal hydride reduction of compound II affords compound III quantitatively.

Ethyl ([2-methyl-2-(4-methylpent-3-en-1-yl)cyclopropyl]methy)carbamate

1-[2-methyl-2-(4-methylpent-3-en-1-yl)cyclopropyl] methanamine (20.0 g, 0.12 mol) in 150 mL of ethyl acetate and ethylchloroformate (17.9 g, 0.165 mol) were charged to a reaction flask. The reaction mixture was then cooled to 0° C. Triethylamine (23.8 g, 0.165 mol) was slowly added while maintaining the reaction temperature at 0° C. Once the feed was complete the reaction mixture was aged for 2 hours than quenched with saturated sodium chloride solution. Kugelrohr distillation afforded 19.2 g of the product, 67% yield. $^1$H NMR (500 MHz, $CDCl_3$) S: 0.07-0.12 (m, 1H), 0.44-0.49 (m, 1H), 0.75-0.79 (m, 1H), 1.04-1.06 (2s, 3H), 1.24 (t, J=6.89 Hz, 3H), 1.24-1.42 (m, 1H), 1.29-1.42 (m, 1H), 1.61 (s, 3H), 1.69 (s, 3H), 2.04-2.08 (m, 2H), 2.99-3.35 (m, 2H), 4.11 (q, J=6.82 Hz, 2H), 4.62 (br. s, 1H), 5.07-5.13 (m, 1H).

Example III

The following reaction sequence was used to make the compound described by the NMR data set forth below:

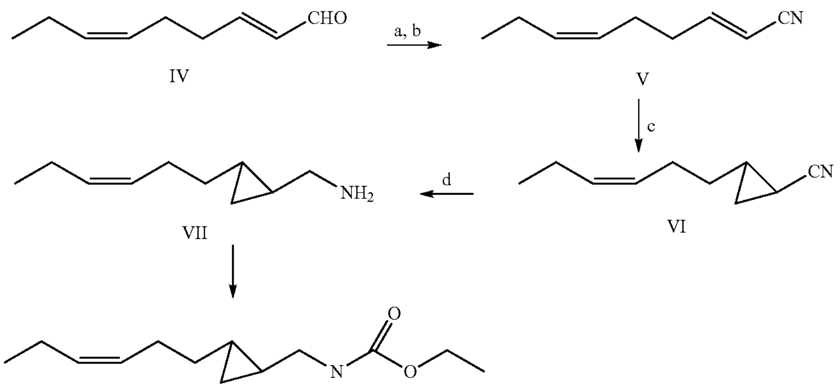

IV
V
VI
VII a) $NH_2OH$, IPA
b) $Ac_2O$, Fe $(Gluc)_2$
c) $Me_3SOI$, NaH, DMSO
d) $LiAlH_4$, IPA

Ethyl (2-[(3Z)-hex-3-en-1-yl]cyclopropyl)methyl) carbamate

Compound IV is a commercially available starting material (AVAILABLE from Bedoukian Research). The conversion of IV to V is a known transformation, which proceeds via an oxime intermediate. Subsequent transformations to the final product follow a similar synthetic scheme to that of example II 1-(2-[(3Z)-hex-3-en-1-yl]cyclopropyl)methanamine 1 eq 1.4 eq of ethylchloroformate, 1.4 eq of triethylamine, quenched with saturated sodium chloride solution, 70% yield. $^1$H NMR (500 MHz, $CDCl_3$) δ: −0.12-0.63 (m, 2H), 0.67-0.74 (m, 1H), 0.81-0.88 & 0.95-0.99 (m, 1H), 0.96 (td, J=7.53, 1.09 Hz, 3H), 1.18-1.29 & 1.44-1.51 (m, 1H), 1.24 (t, J=7.06 Hz, 3H), 1.30-1.39 (m, 1H), 1.98-2.08 (m, 2H), 2.09-2.17 (m, 2H), 3.01-3.05 (m, 1H), 3.11-3.24 (m, 1H), 4.11 (q, J+6.50 Hz, 2H), 4.60-4.77 (br.s, 1H), 5.31-5.47 (m, 2H).

Example IV

Use of the Compound for Umami Enhancement

A trained panel of flavorists and scientists were given a series of paired taste samples containing by weight 0.3% NaCl, 0.1% MSG and 0.015% ribotides. For each member of the panel two samples were prepared. One sample given was the unaltered taste solution, the second sample was the sample one with the addition of 10 parts per million of the above molecules. The panelists found the samples containing the molecules to have higher umami character; the increase in umami perception was increased by up to about 20%.

Example V

Use of the Compounds as Salt Enhancer

An expert panel of flavorists and food technologists were asked to blindly evaluate a series of reduced sodium beef broths containing between five and ten ppm of the molecules of this invention set forth above. The broths were prepared such that the sodium was the same in each broth, meaning that the broths containing molecules had less or no MSG, but had sodium chloride added to ensure the same sodium concentration. The broths were compared with versus without addition of compound. The panel found the broths, to be significantly higher in umami mouthfeel and to be perceivable as more salty. This demonstrates that the molecules can replace MSG and the sodium taste that MSG carries.

Example VI

Use of the Compounds as Salt Enhancer in Spray Dry Form

A spray dry was made using the preferred molecules of the invention as below.

| | |
|---|---|
| Water | 1000 parts |
| Starch Capsul 6330 | 225 parts |
| Mor-Rex 1918 (Maltrin 100) | 900 parts |
| Preferred Molecule (20% in triacetin) | 1000 parts |

Homogenized the mixture and then and fed to drier while on homogenize.
An MSG replacement flavor was made as follows:

| | |
|---|---|
| Above Spray dried composition | 300 parts |
| Salt | 725 parts |
| Ammonium Glycyrrizinate Magnasweet | 1002 parts |
| Mor-Rex 1918 (Maltrin 100) | 150 parts |

The MSG replacer was used at 0.1 to 0.5% in place of MSG at 0.05-0.25%.

What is claimed is:

1. A consumable material selected from the group consisting of a beverage, a foodstuff, a chewing gum, and a dental and oral hygiene product comprising an organoleptically acceptable level of a compound of the formula:

Structure III

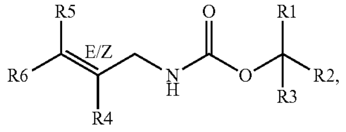

wherein $R^1$ is H;

$R^2$ is selected from the group consisting of H and $C_1$-$C_4$ alkyl;

$R^3$ is selected from the group consisting of H and $C_1$-$C_{10}$ straight or branched chain alkyl and alkenyl;

and $R^2$ and $R^3$ taken together can also represent cyclopropyl;

$R^4$ is H;

$R^5$ is methyl; and $R^6$ is selected from the group consisting of H and $C_1$-$C_9$ straight or branched chain alkyl and alkenyl.

2. The consumable material of claim 1, wherein the compound has the structure:

Structure IV

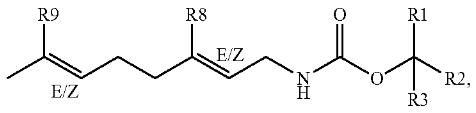

and wherein $R^1$ is H;

$R^2$ is selected from the group consisting of H and $C_1$-$C_4$ alkyl;

$R^3$ is selected from the group consisting of H and $C_1$-$C_9$ straight or branched chain alkyl and alkenyl;

$R^8$ is methyl; and $R^9$ is H or methyl.

3. The consumable material of claim 1, wherein the compound is selected from the group consisting of:

N-[(2E)-3,7-Dimethyl-2,6-octadienyl]-carbamic acid, ethyl ester;

N-[(2E)-3,7-Dimethyl-2,6-octadienyl]-carbamic acid, isopropyl ester;

N-[(2E)-3,7-Dimethyl-2,6-octadienyl]-carbamic acid, allyl ester; and

N-[(2Z)-3,7-Dimethyl-2,6-octadienyl]-carbamic acid, ethyl ester.

4. The consumable material of claim 1, wherein the organoleptically acceptable level of the compound is greater than 50 parts per billion by weight.

5. The consumable material of claim 1, wherein the organoleptically acceptable level of the compound is from about 0.01 parts per million to about 50 parts per million by weight.

6. A method of enhancing the umami flavor or the salty taste of a beverage, a foodstuff, a chewing gum, and a dental and oral hygiene product comprising the step of adding a compound of the formula:

Structure III

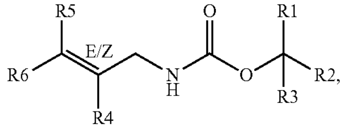

wherein $R^1$ is H;

$R^2$ is selected from the group consisting of H and $C_1$-$C_4$ alkyl;

$R^3$ is selected from the group consisting of H and $C_1$-$C_{10}$ straight or branched chain alkyl and alkenyl;

and $R^2$ and $R^3$ taken together can also represent cyclopropyl;

$R^4$ is H;

$R^5$ is methyl; and $R^6$ is selected from the group consisting of H and $C_1$-$C_9$ straight or branched chain alkyl and alkenyl.

7. The method of claim 6, wherein the compound has the structure:

Structure IV

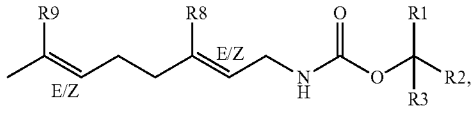

and wherein $R^1$ is H;

$R^2$ is selected from the group consisting of H and $C_1$-$C_4$ alkyl;

$R^3$ is selected from the group consisting of H and $C_1$-$C_9$ straight or branched chain alkyl and alkenyl;

$R^8$ is methyl; and $R^9$ is H or methyl.

8. A combination of (a) a compound of the formula:

Structure III

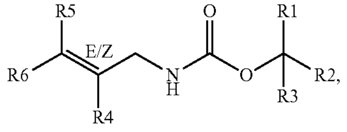

wherein $R^1$ is H;

$R^2$ is selected from the group consisting of H and $C_1$-$C_4$ alkyl;

$R^3$ is selected from the group consisting of H and $C_1$-$C_{10}$ straight or branched chain alkyl and alkenyl;

and $R^2$ and $R^3$ taken together can also represent cyclopropyl;

$R^4$ is H;

$R^5$ is methyl; and $R^6$ is selected from the group consisting of H and $C_1$-$C_9$ straight or branched chain alkyl and alkenyl; and (b) an additional salt taste enhancing material, wherein the weight ratio of (a) to (b) is from 1 to 10 to from 10 to 1.

9. The combination of claim 8, wherein the compound has the structure:

Structure IV

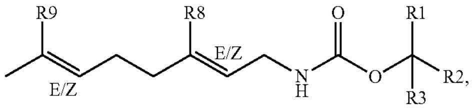

and wherein $R^1$ is H;

$R^2$ is selected from the group consisting of H and $C_1$-$C_4$ alkyl;

$R^3$ is selected from the group consisting of H and $C_1$-$C_9$ straight or branched chain alkyl and alkenyl;

$R^8$ is methyl; and $R^9$ is H or methyl.

10. The combination of claim 8, wherein the weight ratio of (a) to (b) is from about 1 to 3 to about 3 to 1.

11. The combination of claim 8, wherein the weight ratio of (a) to (b) is about 1 to 1.

12. A combination of sodium chloride and an organoleptically acceptable level of a compound of the formula:

Structure III

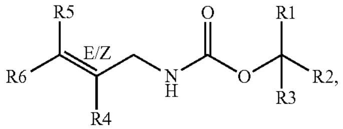

wherein $R^1$ is H;

$R^2$ is selected from the group consisting of H and $C_1$-$C_4$ alkyl;

$R^3$ is selected from the group consisting of H and $C_1$-$C_{10}$ straight or branched chain alkyl and alkenyl;

and $R^2$ and $R^3$ taken together can also represent cyclopropyl;

$R^4$ is H;

$R^5$ is methyl; and $R^6$ is selected from the group consisting of H and $C_1$-$C_9$ straight or branched chain alkyl and alkenyl.

13. The combination of claim 12, wherein the compound has the structure:

Structure IV

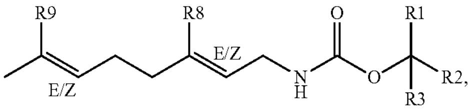

and wherein $R^1$ is H;

$R^2$ is selected from the group consisting of H and $C_1$-$C_4$ alkyl;

$R^3$ is selected from the group consisting of H and $C_1$-$C_9$ straight or branched chain alkyl and alkenyl;

$R^8$ is methyl; and $R^9$ is H or methyl.

14. The combination of claim 12 further comprising an additional salt substitute compound.

15. The combination of claim 14, wherein the additional salt substitute compound is selected from the group consisting of potassium chloride, a ribonucleotide, a cationic amino acid, a low molecular weight dipeptide, monosodium glutamate, a yeast, arginine hydrochloride, arginine ammonium chloride, lysine hydrochloride, and lysine-ornithine hydrochloride.

16. The combination of claim 12 provided to a beverage, a foodstuff, a chewing gum, and a dental and oral hygiene product at a level of greater than 50 parts per billion by weight.

* * * * *